United States Patent
Haas et al.

(10) Patent No.: US 10,593,511 B2
(45) Date of Patent: Mar. 17, 2020

(54) METHOD OF DETERMINING THE DEFLECTION OF AN ELECTRON BEAM RESULTING FROM AN ELECTRIC FIELD AND/OR A MAGNETIC FIELD

(71) Applicant: COMMISSARIAT A L'ENERGIE ATOMIQUE ET AUX ENERGIES ALTERNATIVES, Paris (FR)

(72) Inventors: Benedikt Haas, Grenoble (FR); David Cooper, Grenoble (FR); Jean-Luc Rouviere, Meylan (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 57 days.

(21) Appl. No.: 15/703,557

(22) Filed: Sep. 13, 2017

(65) Prior Publication Data
US 2018/0076005 A1 Mar. 15, 2018

(30) Foreign Application Priority Data
Sep. 14, 2016 (FR) ..................... 16 58594

(51) Int. Cl.
*H01J 37/244* (2006.01)
*H01J 37/26* (2006.01)
(Continued)

(52) U.S. Cl.
CPC ........ *H01J 37/244* (2013.01); *G01N 23/2055* (2013.01); *G01N 23/20058* (2013.01);
(Continued)

(58) Field of Classification Search
CPC .......... G01N 23/20058; G01N 23/2055; H01J 2237/2614; H01J 2237/2805; H01J 37/244; H01J 37/268; H01J 37/2955
See application file for complete search history.

(56) References Cited

U.S. PATENT DOCUMENTS

2011/0049363 A1 3/2011 Koch
2011/0220796 A1 9/2011 Nicolopoulos et al.
(Continued)

FOREIGN PATENT DOCUMENTS

EP 3 032 244 A1 6/2016

OTHER PUBLICATIONS

French Preliminary Search Report dated May 9, 2017 in French Application 16 58594 filed on Sep. 14, 2016 (with English Translation of Categories of Cited Documents).
(Continued)

*Primary Examiner* — Nicole M Ippolito
*Assistant Examiner* — Sean M Luck
(74) *Attorney, Agent, or Firm* — Oblon, McClelland, Maier & Neustadt, L.L.P.

(57) ABSTRACT

A method of determining a local electric field and/or a local magnetic field in a sample and/or the dielectric constant of a material and/or the angle between the input and output surfaces of the sample, comprising illumination of the sample by an electron beam in precession mode using an illumination device, generation of a diffraction pattern, determination of the offset of the disk corresponding to the transmitted beam due to the electric field and/or the magnetic field, by comparison of the diffraction pattern and a reference diffraction pattern, determination of a deflection angle of the transmitted beam, and determination of the value of the local electric field and/or the local magnetic field of the sample and/or determination of the dielectric constant of materials and/or determination of the angle between the input and output surfaces of the sample.

20 Claims, 6 Drawing Sheets

(51) Int. Cl.
*H01J 37/295* (2006.01)
*G01N 23/20058* (2018.01)
*G01N 23/2055* (2018.01)
*G01R 33/02* (2006.01)
*G01N 27/06* (2006.01)
*G01R 29/08* (2006.01)

(52) U.S. Cl.
CPC ............. *G01N 27/06* (2013.01); *G01R 29/08* (2013.01); *G01R 33/02* (2013.01); *H01J 37/268* (2013.01); *H01J 37/2955* (2013.01); *H01J 2237/2614* (2013.01); *H01J 2237/2805* (2013.01)

(56) References Cited

U.S. PATENT DOCUMENTS

| 2012/0025094 A1 | 2/2012 | Benner et al. | |
|---|---|---|---|
| 2013/0206968 A1 | 8/2013 | Rouviere | |
| 2013/0240728 A1* | 9/2013 | Albiol .................... | H01J 49/44 250/305 |
| 2015/0076346 A1 | 3/2015 | Weiss et al. | |

OTHER PUBLICATIONS

Mihaela Tanase et al. "In Situ TEM Observation of Magnetic Materials," Microscopy Reasearch and Technique 72; 2009, pp. 10.

Thibaud Denneulin et al. "Differential phase-contrast dark-field electron holography for strain mapping." Ultramicroscopy, 160. 2016. pp. 12.

Naoya Shibata et al., "Differential phase-contrast microscopy at atomic resolution", Nature Physics, Letters, vol. 8, Jun. 2012, pp. 5.

Kayla X. Nguyen et al. "Lorentz-STEM imaging of Fields and Domains using a High-Speed, High-Dynamic Range Pixel Array Detector at Atomic Resolution". Microsc. Microanal. 21 (Suppl 3), 2015, pp. 2.

R. Vincent et al. "Double conical beam-rocking system for measurement of integrated electron diffraction intensities", Ultramicroscopy 53, Jul. 1994, pp. 12.

Knut Muller et al. "Strain Measurement in Semiconductor Heterostructures by Scanning Transmission Electron Microscopy". Microscopy and Microanalysis, 2012, pp. 15.

Jean-Luc Rouviere et al. "Improved strain precision with high spatial resolution using nanobeam precession electron diffraction", Applied Physics Letters 103, 2013, pp. 5.

Yifeng Liao et al. "Reduction of electron channeling in EDS using precession", Ultramicroscopy 126, 2013, pp. 4.

Dirk Padfield, "Masked Object Registration in the Fourier Domain," IEEE Transactions on Image Processing, vol. 21, No. 5, May 2012, pp. 13.

Edward A. Lewis et al. "Real-time imaging and local element analysis of nanostructures in liquids". Chemical Communication, 50, 10019, 2014, pp. 5.

David B. Williams, et al., "Transmission Electron Microscopy", 2nd edition, Springer, 2009, pp. 20.

* cited by examiner

METHOD OF DETERMINING THE DEFLECTION OF AN ELECTRON BEAM RESULTING FROM AN ELECTRIC FIELD AND/OR A MAGNETIC FIELD

TECHNICAL DOMAIN AND STATE OF PRIOR ART

This invention relates to a method of determining the deflection of an electron beam resulting from a local electric field and/or a local magnetic field and a method of determining the value of said local electric field and/or local magnetic field in a sample and/or the properties and/or characteristics of a sample.

It is interesting to be able to detect and quantify local electric fields and magnetic fields with a nanometric resolution in different media. Knowledge of the presence and values of these fields can provide information about phenomena that generate such fields, for example such as the piezoelectric effect, accumulation of charges, dopant gradients, the presence of depletion zones.

The presence of an electric field or a magnetic field deviates the trajectory of an electron beam. By determining this deviation or deflection, the value of the electric field or the magnetic field, or other properties and/or characteristics of the sample can be determined if the value of the electric field or the magnetic field is known.

There are several methods of measuring this influence and therefore for determining for example the values of these fields, including the electronic holograph, either off or on the axis, that can achieve a nanometric resolution. But this method has spatial resolution problems. It is also complex to implement There is also the method called the Differential Phase Contrast (DPC) method that uses segmented annular detectors comprising pairs of opposite segments.

This method is described for example in the document by Shibata et al, *Differential phase-contrast microscopy atomic resolution, Nature Phys.* VOL. 8-pp 611-615 (2012). Deflection of the electron beam due to the presence of an electric or magnetic field is detected by taking the difference between measurements obtained for opposite segments of the detector. This method is relatively easy to implement but its sensitivity is low, it is not easily quantitative and it is very sensitive to the effects of diffraction.

Another method that measures the centre of gravity of the disk of the beam transmitted in diffraction mode described in the document by Nguyen et al, *Lorentz-STEM imaging of Fields and Domains using a High-Speed, High-Dynamic Range Pixel Array Detector at Atomic Resolution, Microsc and Microanal.* 21 (Suppl 3), 2015 pp 2309-2310 provides better results. However, it suffers from lack of precision due to the superposition of diffracted and transmitted beams and/or intensity variations in these beams.

PRESENTATION OF THE INVENTION

Consequently, one purpose of this invention is to disclose a precise method with nanometric resolution, capable of determining the effect of a local electric field and/or a local magnetic field and a sample on an electron beam, particular on the deflection of this electron beam, determination of this effect in particular making it possible to determine the value of the local electric field and/or the local magnetic field or the properties of a sample with a nanometric resolution.

The purpose of this invention is achieved by a method of determining the deflection of an electron beam resulting from a local electric field and/or a local magnetic field and the presence of a sample, comprising the following steps:

placement of a sample and illumination of a zone of the sample in which it is required to determine the effect of the electric field and/or the magnetic field by an electron beam in precession mode, generation one or several diffraction patterns, analysis of the diffraction pattern(s) to measure the offset of the disk corresponding to the transmitted beam and/or the diffracted beams or the reflected beam, determination of the deflection angle of the transmitted electron beam and/or diffracted beams or the reflected beam relative to the incident beam.

In this application, the "diffraction pattern" refers to all signals collected by a multichannel detector comprising at least 4 channels or pixels, that gives information about directions in which particles of the incident beam propagate after their interaction with the sample. In a transmission microscope, this information is traditionally obtained in "diffraction" mode in which the position of the detector is conjugated with the focal plane of the objective lens. A diffraction pattern comprises a transmitted disk and diffracted disks or a disk due to the reflected beam.

The method can be used to measure the projection perpendicular to the electric field and/or the magnetic field internal to a material. Conversely, if either or both of these fields is (are) known and the value of the deviation is determined, other properties of the sample can be determined, for example such as its dielectric strength, its refraction index, its bevel angle, etc.

Precession mode means that the incident beam makes at least one revolution, the incident beam forming an angle from the optical axis of the microscope, and generates a precession cone. The angle may or may not be constant. In the case of a symmetric precession cone generated by a circle, the cone angle is called the precession angle.

Illumination by an electron beam in precession mode provides a mean of averaging several incidence directions, the diffraction disks obtained are then more uniform in intensity. In particular, interference contrasts due to coherent diffraction are attenuated or disappear and diffraction disks with homogeneous intensity with well-defined contours are then obtained, so that their position and therefore the offset between disks of several diffraction patterns can be measured precisely, and thus the influence of the electric field and/or the magnetic field on the electron beam can be measured and the value of the electric field and/or the magnetic field can be deduced from this measurement.

Preferably, the information on the transmitted beam is used to measure the electric/magnetic fields and other properties such as the bevel angle.

Very advantageously, measurements are made in a vacuum without an electric or magnetic field or on a uniform sample with no field. These measurements are then "subtracted" from measurements made in the zone in which it is desired to make measurements, particularly to delete parasite deflections that occur when the beam is translated.

It is possible to make additional measurements on diffraction patterns such as stress measurements in crystalline materials from first and second order diffracted disks.

The position of disks in the transmitted beam can advantageously be detected by software that automates the method.

It is also possible to make measurements at different points in the zone.

The subject-matter of this invention is then a method of determining the deflection of an electron beam resulting from an electric field and/or a magnetic field and the presence of a sample, the incident electron beam having an initial direction, comprising the following steps:

a) placement of a sample and illumination of the sample by an electron beam in precession mode using an illumination device, b) generation of at least one diffraction pattern, c) analysis of the at least one diffraction pattern to measure an offset of a disk corresponding to the transmitted beam and/or the diffracted beams or the reflected beam, d) determination of the deflection of the electron beam due to the sample relative to the initial direction from the offset of said disk obtained in step c).

Advantageously, the method comprises a step e) prior to step c) to make at least one diffraction pattern in a vacuum or a diffraction pattern with another sample and the offset in step c) is obtained by comparing the diffraction patterns of steps b) and e).

For example, in precession mode, the electron beam forms an angle of between 0.01° and 10°. The angle of the incident electron beam can vary.

Preferably, each diffraction pattern is produced using data supplied during at least one revolution, and preferably during several revolutions.

The method advantageously comprises a step a1) between steps a) and b) of dynamic compensation of the tilt due to precession mode.

In one example embodiment, step c) applies a cross correlation to determine the offset.

Preferably, during step a), the diameter of the incident electron beam is between 0.1 nm and 100 nm and/or the energy of the incident electron beam is between 1 keV and several MeV.

Steps a), b), c) and d) are for example done in n zones of the sample and step e) is done in p zones, where p is less than n, and a step to extrapolate to n zones is done.

Offsets between two orthogonal directions can be measured during step c).

Another subject-matter of this invention is a method of determining the value of the local electric field and/or the value of the local magnetic field of said sample applying the determination method according to the invention, said method also including a step f) to determine the local electric field and/or the local magnetic field of said sample starting from the deflection angle determined in step d).

The sample may comprise a bevel angle with a known value, comprising the step to determine the optical index of the sample from the value of the deflection angle of the incident beam and the step to calculate the value of the local electric field and/or the value of the local magnetic field from the value of the optical index and the bevel angle.

Another subject-matter of this invention is a method of determining the properties of the sample applying the determination method according to the invention, and knowledge of the electric and/or magnetic field, for example the dielectric constant of the sample or its internal potential.

Another subject-matter of this invention is a method of determining the chemical composition of a sample including application of the determination method according to the invention and performing an EDX experiment.

Another subject-matter of this invention is a method of determining the dielectric constant of a liquid sample applying the determination method according to the invention, an electric field and/or a magnetic field with known values being applied.

Another subject-matter of this invention is a method of determining the bevel angle of a sample applying the determination method according to the invention, the value of the local electric field and/or the value of the local magnetic field of the sample being known.

BRIEF DESCRIPTION OF THE DRAWINGS

This invention will be better understood after reading the following description and the appended drawings on which.

DETAILED PRESENTATION OF PARTICULAR EMBODIMENTS

The invention relates to a method of determining the deflection angle of an electron beam due to the presence of a local electric field and/or a local magnetic field in an environment in which diffraction by an electron beam is possible, either by transmission or by reflection. In the latter case, the electron beam does not pass through the sample, therefore the sample does not have to transparent to electrons.

It can for example be a crystalline or amorphous solid environment, for example a semiconducting material, a liquid environment, a gas environment, for example to determine for example the dielectric constant or vacuum.

For reasons of simplicity, the term "sample" refers to the environment in which the effect on deflection of the electron beam is to be measured. The term "field" is used to designate both the local electric field and the local magnetic field except when it will be useful to make a distinction between them.

As explained below, this invention can for example be used to determine the component of the electric field or the magnetic field that deviates the incident electron beam that is the transverse component. For reasons of simplicity, the remainder of the description will refer to determination of the field in general.

Figure 1:
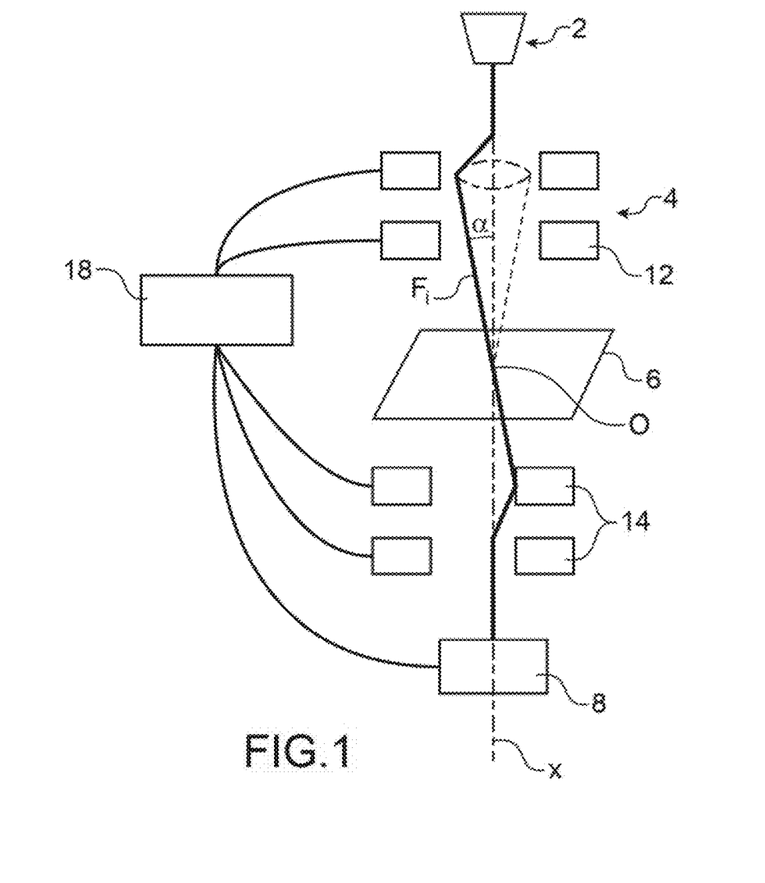
FIG. 1 is a diagrammatic view of an example of a system for implementing the determination method according to the invention.

FIG. 1 shows a diagrammatic view of a system for implementing the determination method according to the invention.

The measurement system comprises an electron microscope (EM) 2, either in transmission (TEM) or in reflection (SEM), means of illuminating in precession mode 4, a sample holder 6 and means 8 of collecting transmitted and diffracted or reflected beams and obtaining diffraction patterns. The system also includes means 10 of processing the diffraction patterns and, in one example embodiment, means of determining the value of the local electric field or the local magnetic field in the sample.

The electron microscope is advantageously capable of generating an electron beam with nanometric diameter with a small angle of convergence, which can give diffraction patterns on which the transmitted disk and the diffracted disks do not superpose or their superposition is minor and gives better precision. The diameter at mid-height of the beam can vary from 0.1 nm to 100 nm and the convergence angle can vary between about 0.0057° (0.1 mrad) and about 5.7° (100 mrad). Preferably, the energy of the beam is then between 1 keV and several MeV.

One example of such a system is well known to an expert in the field and is described for example in document US2015/0076346.

The means of illuminating in precession mode 4, for example coils 12, upstream the sample holder 6 that are electrically powered to control the deflection angle $\alpha$ of the incident beam Fi relative to the optical X axis, called the half-precession angle such that as the incident beam moves, it generates a precession cone C as shown on FIG. 1. The fixed point O about which the incident beam Fi rotates corresponds to the analysed zone of the sample. Values of $\alpha$ can vary from 0.01° to 10° and preferably between 0.1° and 1°.

Advantageously, the means of making illumination in precession mode 4 comprise means of compensating the effect of deflection of the incident beam Fi on the transmitted beam. For example, these compensation means comprise coils 14 behind the sample-holder that are electrically powered so as to compensate for the effect of deflection of the incident beam F on the transmitted beam. This compensation is also called "descan" correction.

As a variant, the precession function can be made by rotating the sample.

As a variant on the compensation, it can be envisaged to make this compensation by processing of signals measured using a shape recognition algorithm that uses cross-correlation.

In one example embodiment, the means 8 of collecting the transmitted beam and possibly the diffracted beams or possibly the reflected beam, comprise for example a Charge Coupled Device (CCD) type camera or any other network of detectors in two dimensions with sufficient sampling, such as CMOS detectors located downstream the sample-holder.

According to another example embodiment, the detector can be composed of four detectors for example in the form of a circle or a ring divided into four equal sectors on which the beam is initially centred.

The coils 12 and 14 are connected to a control unit 18, as the CCD camera 8.

We consider a system comprising a TEM. The measurement method according to this invention includes the following steps, after placement of the sample on the sample holder.

a) illumination of the sample by the electronic beam in precession mode, b) collect transmitted and diffracted beams and generate at least one diffraction pattern, c) treatment of said diffraction pattern to determine the offset of the disk derived from the transmitted beam and/or the diffracted beams or the reflected beam, d) determination of the deflection angle.

In this application, we refer to the offset of the disk corresponding to the transmitted beam and/or the diffracted beams or the reflected beam, This offset is measured either relatively, if no measurement has been made without a sample, or absolutely if measurements have been made without samples. In the case of a relative measurement, it is determined how the position of the disk varies when the electron beam scans the zone of interest. Relative measurements show how fields vary within the zone of interest, but there is no absolute quantitative measurement of the fields. Absolute measurements determine the value of the fields. Furthermore, absolute measurements can be used to eliminate parasite offsets that are often introduced when scanning the beam. In some cases, for example, if a relative measurement is sufficient and/or if measured offsets are greater than parasite offsets introduced by scanning, a reference measurement is not necessary.

During step a) the coils are powered to start movement of the incident beam Fi such that it passes through a precession cone with precession angle $\alpha$ relative to the optical X axis of the microscope. The angle $\alpha$ can be constant, the cone is then a cone of revolution, i.e. generated by a circle.

As a variant, a can vary during the measurement, the cone can then have any base, for example an elliptical base that would have the effect of giving more spatial resolution in one direction, because precession increases the size of the probe slightly.

For example, electronic diffraction in precession mode is described in the document by R. Vincent, P. A. Midgley "*Double conical beam-rocking system for measurement of integrated electron diffraction intensities*", Ultramicroscopy, 53 (1994) 271-282.

The TEM is adjusted such that the electron beam, and more particularly the point O around which the electron beam rotates is close to the input face, i.e. the face that receives the incident beam, of the zone to be measured. The optimum spatial resolution is obtained when point O is located on this input face.

For each diffraction pattern, the electron beam makes at least one revolution. Preferably, the beam makes several revolutions to give better homogeneity.

Transmitted and diffracted beams are advantageously compensated to be stationary in the diffraction space. They are collected by the CCD camera and are used to create diffraction patterns. The work in the reciprocal space and not in the real space has several advantages. Firstly, deflection of the incident beam due to the presence of the field and proportional to the intensity of this field causes a displacement of the transmitted beam in the reciprocal space, and this displacement can then be used to determine the field intensity. Secondly, the position of diffraction spots in the reciprocal space is not affected by offsets due to scanning of the beam at the surface of the sample in the direct space, because an offset of the beam in the direct space results in phase shifts in the diffracted beams, that cannot be seen because the detector only records the intensities of the diffracted beams. Risks of having incorrect measurements are lower.

Furthermore, dynamic compensation of transmitted and diffracted beams can very significantly reduce coherent diffraction contrasts inside diffraction disks and obtain diffraction disks with a uniform intensity and therefore with well-defined edges that are easy to detect.

Furthermore, by choosing a beam with a sufficiently low convergence angle, for example within the interval given above, for example equal to about 0.057° (1 mrad), the transmitted beam and the diffracted beams correspond to disks on the diffraction patterns in the reciprocal space, while in the real space they have complex and diffuse shapes. Consequently, displacement of the disk due to the influence of the field is more easily measurable because disk contours are relatively well-defined due to illumination in precession mode. Even in the case of amorphous materials with a strongly diffuse background, the transmitted disk remains discernable and useable. In the case of crystalline materials, the transmitted disk or a diffracted disk can be used. However, the use of a diffracted disk is more complex because there is no reference of diffracted disks in a vacuum and strain effects can be added. Advantageously, the centre of gravity of two disks symmetric about the transmitted beam can be used to eliminate the effects of strain.

This makes it possible to work in reflection mode when there are no transmitted beams.

Thus, the positions of disks of the transmitted beam or several diffracted disks can be detected precisely and compared so as to determine the offset specifically due to the fields. Therefore, determination of the field intensity is also made more precise.

The position of transmitted and/or diffracted disks is measured on the two-dimensional detector. Possible rotation between the observed sample and the detector is taken into account.

It would then be possible to envisage calculating the offset in only one direction and having a value of the field, for example when the direction of the field is known.

Measurements in two orthogonal directions can also determine the orientation of the field in the plane.

In the case of a two-dimensional detector, the offset of the disk of the transmitted beam is advantageously calculated automatically using an algorithm called by software. For example, the algorithm uses image cross-correlation to optimise determination of displacements of the transmitted beam. Alternatively, other methods to precisely detect the position of diffraction spots applicable to this invention are described in the document by K. Müller, A. Rosenouer, M. Schowalter, J. Zweck, R. Fritz, K. Volz, "*Strain measurement in semiconductor heterostructures by scanning transmission electron microscopy*", Microsc. Microanal. 18 (2012) 995-1009.

In the case of a detector with 4 segments, the offset of the transmitted beam disk can be measured using known DPC methods, i.e. by comparing the signals from two opposite segments. Intensity variations between the 4 sectors can be used to measure the offset of the transmitted beam. The use of a detector with 4 segments has the advantage that it is faster than a method using a CMOS detector, because there are only 4 pixels to be processed. However, this method is less precise.

The algorithm can include the following steps.

(1) A particular diffraction pattern is chosen as reference among the series of diffraction patterns in the zone of interest considered.

(2) On the reference pattern, it is chosen to only keep the near region of the transmitted beam, in other words the other tasks on the diffraction pattern are deleted. Typically, the radius of the selected region is equal to g/2 where g is the distance between the transmitted beam and the closest diffraction beam.

(3) A cross correlation between the previous diffraction pattern called the transmitted reference pattern and the pattern to be studied is made. Advantageously, it would be possible to make derivatives (for example by applying a Sobel filter) of the transmitted reference pattern and the pattern(s) to be studied before making the correlation product, making it more sensitive to the position of the contour. The position of the maximum of this cross correlation image gives the offset of the transmitted beam directly. This masking is advantageously done using the masked Cross-correlation concept described in the document by Padfield et al, <<*Masked object registration in the Fourrier domain*>> IEEE Transactions on image Processing, 21(5): 2706-2718, 2012.

Very advantageously, the determination method according to the invention includes a measurement step in a vacuum in the absence of a field, i.e. in the absence of the sample, but under the same conditions and when the position of the transmitted beam is measured. The method also comprises a step during which the measurement obtained in the absence of a sample is subtracted from the measurement made with the sample. The physical dimensions of the zone scanned on the sample and the zone scanned in a vacuum are preferably the same. But the zone scanned in a vacuum can comprise fewer points, the missing points being obtained by interpolating the measurements.

A parasite can deviate the beam due to misalignment of the microscope, in a vacuum and in the absence of a field. In general, the parasite deflections associated with scanning of the beam are small if the electron beam scanning system is correctly adjusted. However, deflections introduced by the field(s) are very small, and the result is that parasite deflections are comparatively large.

Therefore these additional steps of measurement in a vacuum advantageously make it possible to completely cancel this artefact. Furthermore, the positions obtained are normalised relative to the position in a vacuum.

We will now show how the field can be determined, from transmitted disk position measurements.

Figure 2:
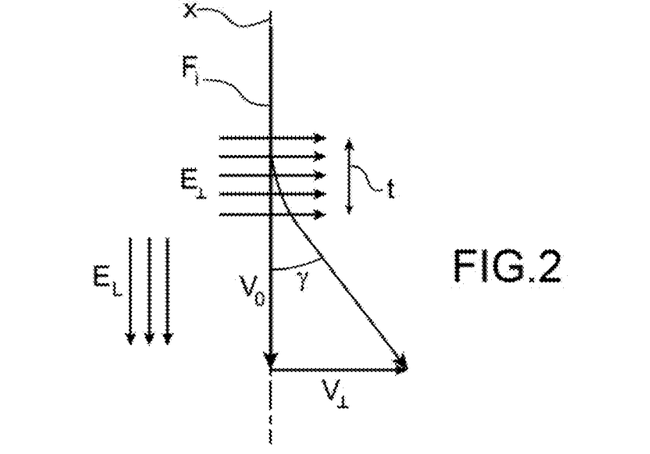
FIG. 2 is a diagrammatic view of an electron beam deviated by an electric field.

The effect of an electric field on an electron beam Fi is shown diagrammatically on FIG. 2.

The electric field is broken down into a longitudinal component $E_t$ parallel to the optical axis of the beam and a component $E_T$ transverse to the optical axis of the beam.

In the first order, only the transverse component $E_T$ has an influence on the direction of the beam FI, the longitudinal component $E_L$ only has an effect on the acceleration or deceleration of electrons. Therefore the method can be used to measure the transverse component $E_T$ of the electric field perpendicular to the electron beam. The sample is turned by a certain angle to measure the longitudinal component $E_L$.

Preferably, the sample is turned by an angle of 90°, but smaller angles for example such as 30° can also be used to measure the longitudinal component.

$F_T$, the component (not shown) of the force applied by the electric field perpendicular to the beam direction, is written as follows:

$$\vec{F}_\perp = q \cdot \vec{E}_\perp$$

Where q is the electric charge of the electron.
$F_T$ can also be written:

$$\vec{F}_\perp = m^*_e \cdot \vec{a}_\perp$$

Where $m^*_e$ is the relativistic mass of the electron and $a_T$ is the component of the average acceleration perpendicular to the direction of the beam. $A_T$ can be written as $a = V_T \times \tau$. Then $$\frac{\vec{F}_\perp}{m_e^+} \cdot \tau = v_\perp$$

Now $\tau = t/v_0$ let t be the distance over which the electric field extends,
let $v_0$ be the initial velocity of electrons in the direction of the beam.
Then $$v_\perp = \frac{E_\perp \cdot q \cdot t}{m_e^+ \cdot v_0}$$

The deflection angle γ due to the effect of the electric field can be written:

$\gamma = \arctan(v_\perp/v_0) \cong v_\perp/v_0$

The result is that:

$$E_\perp = \frac{\gamma \cdot m_e^+ \cdot v_0^2}{q \cdot t} \quad (I)$$

All parameters of equation (I) are known except for γ and t that can be determined.

γ is determined using the measurement method according to the invention from offsets of transmitted disks and t is known or determined for example by methods using a focussed electron probe and a network of 2D detectors in transmission, such as electronic diffraction of a convergent beam or electronic diffraction of a convergent beam with averaged position, as described in "*Transmission Electron Microscopy*", D. B. Williams and C. B. Carter, 2$^{nd}$ edition, Springer, p. 352, or the Energy dispersive spectrometry (EDS) method as described in document EP 3 032 244 A1

For a 200 kV electron beam, equation I is written:

$E_\perp = -\gamma/t \times 3.438 \cdot 10^5 V$

We will not repeat the calculations used to determine the magnetic field. As for the electric field, only the transverse component of the magnetic field can be measured.

We can write:

$$B_\perp = \frac{\gamma \cdot m_e^+ \cdot v_0}{q \cdot t} \quad (II)$$

For a 200 V electron beam, we obtain:

$B_\perp = -\gamma/t \times 1.649 \cdot 10^{-3} T.$

Using the method according to the invention that is capable of determining the value of γ precisely, it is relatively easy to obtain the value of the local electric field or the local magnetic field.

The value of the determined field can be relative by comparing the offset of a diffraction pattern with the offsets measured on other parts of the sample or with offsets measured on another sample, or it can be absolute by comparing it with an offset measured in a vacuum in the absence of a field, this offset in a vacuum is then measured as described below.

The measurement method according to the invention can also be made in several zones of the sample, for example in different planes, considering the optical direction of the microscope and in different positions in each plane. It is thus possible to have a map of values of the field(s) in the sample.

These measurements can easily be made by modifying zones illuminated by the electron beam.

We will now describe an example measurement to determine piezoelectric fields using the determination method according to the invention in a sample comprising structures with several InGaN/GaN quantum wells on a substrate made of GaN(0001).

The sample is thinned so that it can be observed along the axis of the zone [11-20] (Miller-Bravais indexes, the electron beam will be parallel to this direction) that is perpendicular to the piezoelectric direction [0001], for example by "focused ion beam milling".

The transmission microscope used is a Titan3 G2 60-300 Ultimate® operating at 200 kV and the transmitted and diffracted beams are collected by a Gatan UltraScan® CCD camera.

The microscope is adjusted to have a 0.7 nm diameter beam focussed in a vacuum with a convergence angle of 1.8 mrad (0.1°). The precession angle is fixed at 0.25° and the revolution period of the beam is 0.1 s. The exposure time of the CCD camera is 0.4 s equal to 0.4 times the revolution period of the beam. Advantageously, binning or averaging on several pixels is applied to the camera, for example a 512×512 pixel image is obtained for a binning of 4.

The beam current is of the order of 50 pA and the thickness of the sample is of the order of 150 nm.

Preferably, the microscope is adjusted to reduce parasite deflections introduced by scanning of the beam on the sample (adjustment of pivot points in scanning mode) and precession mode is adjusted The sample is placed in the microscope at the optical axis and at the eucentric height.

Scanning is such that it includes multilayers of InGaN/GaN and the GaN located under and above the stack. The sample comprises six layers of InGaN. Scanning is done over a length of 75 nm in steps of 0.5 nm. Scanning consists of 150 points along the stack and 10 points along the perpendicular direction.

Figure 3A:
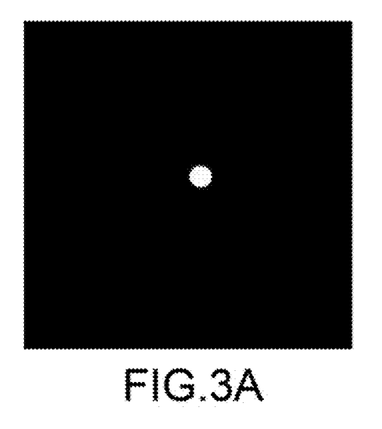
FIG. 3A is a diffraction pattern in the case of a measurement in a vacuum and in the absence of an electric field and/or a magnetic field.
Figure 3B:
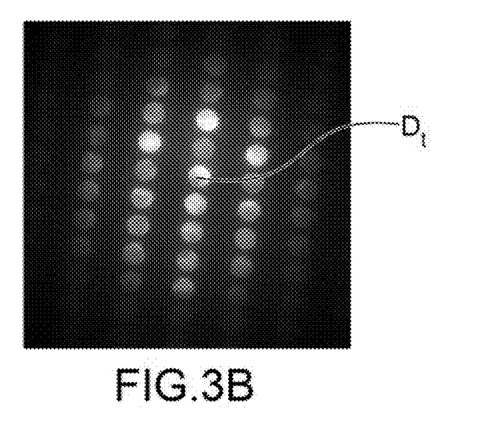
FIG. 3B is a diffraction pattern of an InGaN/GaN sample.

Measurements are made in a vacuum, on a zone of the same size, namely 75 nm by 5 nm. However, the number of points along the stack in a vacuum was reduced to 10. FIG. 3A shows a diffraction pattern for the measurement in a vacuum, all that is visible is the disk of the transmitted beam, and FIG. 3B shows an example of a diffraction pattern of the sample comprising the disk of the transmitted beam Dt and disks of the diffracted beams surrounding the disk Dt.

The offset is measured in the X, Y coordinate system of the detector.

Figure 4A:
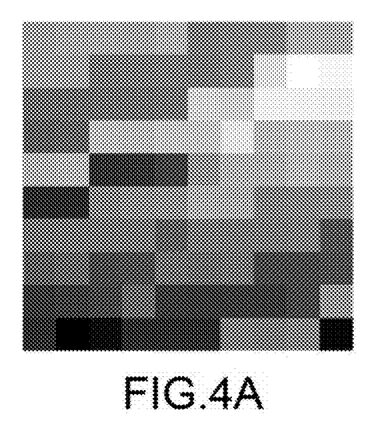
FIG. 4A is a view in grey levels of the offset in X of the disk of the beam transmitted in 10×10 points measured in a vacuum and in the absence of an electric and/or magnetic field.
Figure 4B:
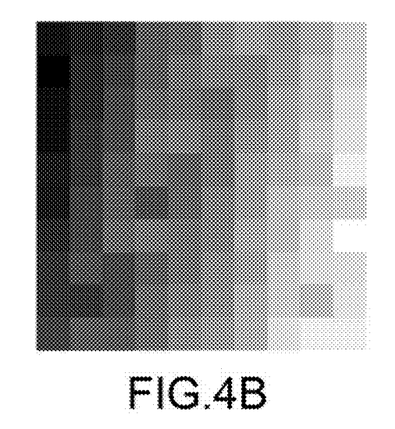
FIG. 4B is a view in grey levels of the offset in Y of the disk of the beam transmitted in 10×10 points measured in a vacuum and in the absence of an electric and/or magnetic field of the sample.

For measurements in a vacuum, the positions of disks in the transmitted beam are measured using the algorithm mentioned above. They are shown on FIGS. 4A and 4B, FIG. 4A showing the offset in X and FIG. 4B showing the offset in Y. The positions of the 150×10 positions, corresponding to scanning on the sample are interpolated from 10×10 experimental positions made in a vacuum The offsets are represented in grey levels, the scale of the grey levels ranging from −3 pixels corresponding to black and +3 pixels corresponding to white.

Measurements are then made on the sample, 150×10 diffraction patterns are made and the positions of transmitted disks are extracted by applying the algorithm for each pattern.

Figure 5A:
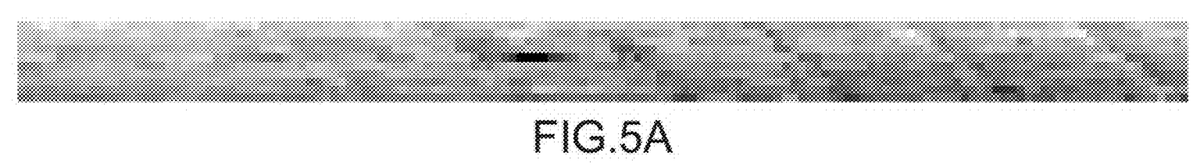
FIG. 5A is a view in grey levels of the offset in X of the disk of the beam transmitted in 150×10 points on the sample.
Figure 5B:
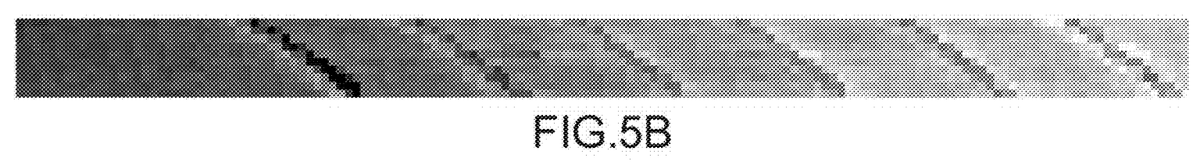
FIG. 5B is a view in grey levels of the offset in Y of the disk of the beam transmitted in 150×10 points on the sample.

Figure SA shows the offset along X of the disk and FIG. 5B shows the offset along Y at the 150×10 measurement positions.

It will be understood that the same number of measurements can be made in a vacuum as in the sample, i.e. 150×10, but it has been observed that satisfactory results are obtained if fewer measurements are made and if they are interpolated, with a saving of data acquisition and processing times.

The next step is to subtract the interpolated offset in a vacuum from offsets along X and along Y.

Figure 6A:
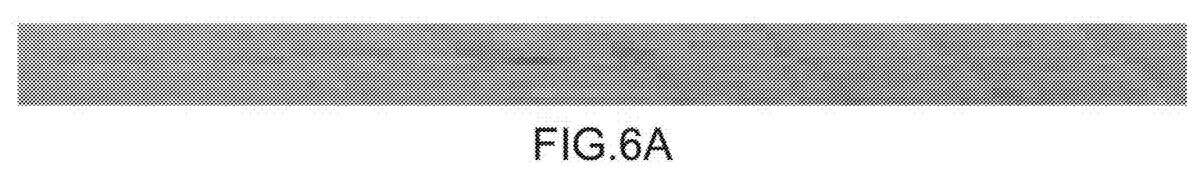
FIG. 6A is a view in grey levels of the offset in X of the disk of the beam transmitted in 150×10 points on the sample, corrected by the offset in X measured in a vacuum in FIG. 4A extrapolated to 150×10 points.
Figure 6B:
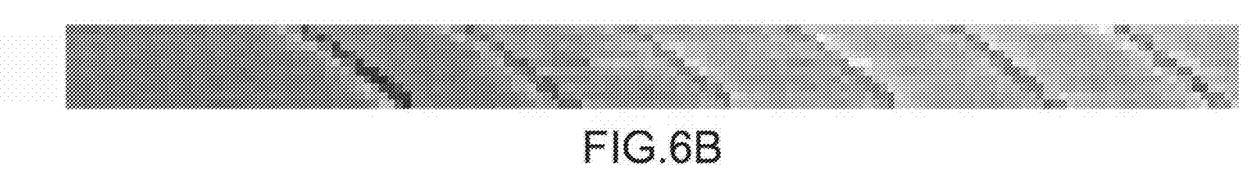
FIG. 6B is a view in grey levels of the offset in Y of the disk of the beam transmitted in 150×10 points on the sample, corrected by the offset in Y measured in a vacuum in FIG. 4A extrapolated to 150×10 points.

The result obtained is corrected offsets along X (FIG. 6A) and along Y (FIG. 6B). These offsets measured in pixels are converted into an angle by calibrating the detector. Traditionally, this is done using a diffraction pattern of a known sample. The next step is to calculate the component $E_T$ of the electric field using equation I. The thickness of the sample t=150 nm, was determined from a diffraction pattern obtained by Convergent Beam Electron Diffraction (CBED).

Figure 7:
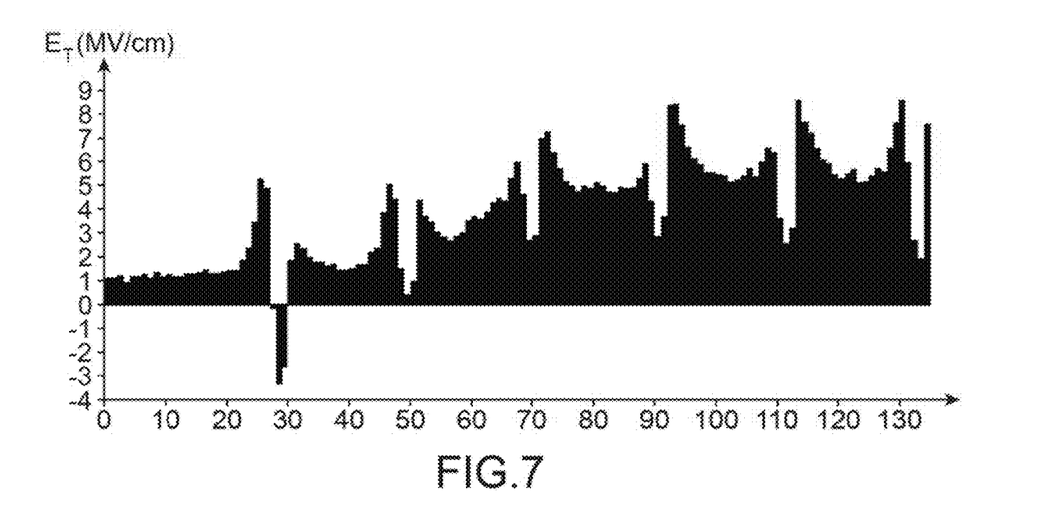
FIG. 7 is a profile of the electric field $E_T$ perpendicular to the electron beam and to the interfaces, calculated in MV/cm and determined from the offset in FIGS. 6A and 6B.
Figure 8:
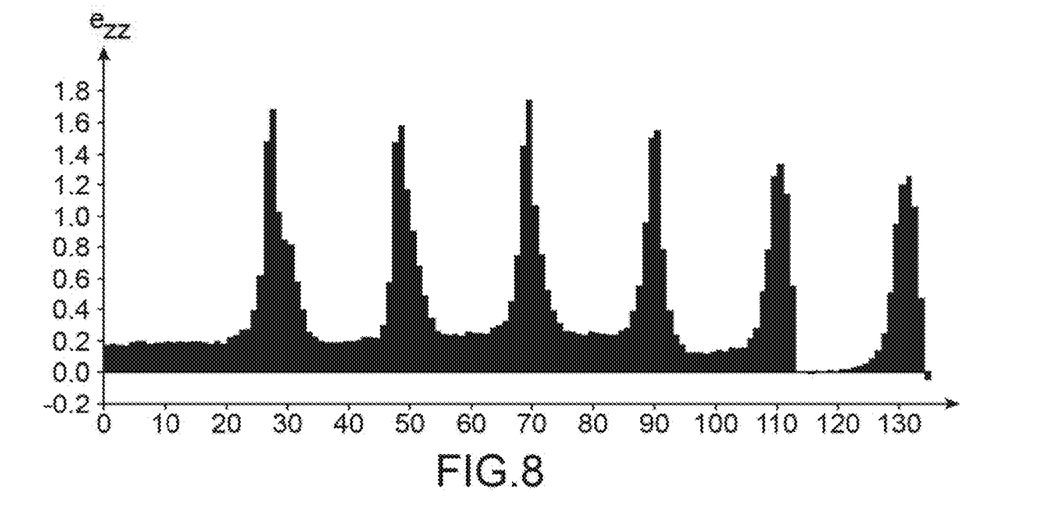
FIG. 8 is a profile of internal strains $e_{zz}$ along the growth direction z as a percentage determined from variations in distances between the transmitted disk and the spot (0002) of the diffraction pattern.

FIG. 7 shows the profile of $E_T$ in MV/cm along the stack of layers.

The method according to the invention has the advantage that it can make mesh parameter measurements at the same times as the electric field measurement, such mesh parameters for example are described in the document by Rouviere et al., "*Improved strain precision with high spatial resolution using nanobeam precession electron diffraction*", *Applied Physics Letters* 103, 241913, or EDX or EDS (Energy Dispersive X-ray Spectrometry) measurements that determine the local chemical composition. EDX measurements made in precession mode are described for example in the document by Liao et al. *Reduction of electron channeling in EDS using precession, Ultromicroscopy* 126 (2013), 19-22.

As indicated above, the method according to the invention using precession mode can reduce the effects of diffraction during the measurements. Since the sample can be oriented along an axis of the zone, the spatial resolution is determined only by the spread of the electron beam in the sample and can be as much as 1 nm.

The method according to the invention can be applied to different sample thicknesses, chosen such that the sample remains transparent to electrons.

Very advantageously, scanning is automated and the treatment of each pattern to determine the offset of the transmitted disk at each position is also done using software implementing the algorithm. The measurements made are then precise and reproducible.

The method according to the invention can give a quantitative distribution of electric and magnetic field components perpendicular to the electron beam. It can also create maps of internal potentials, potentials due to dopants, and piezoelectric and ferroelectric fields present in the sample.

It can also be envisaged to apply this method while applying stresses to the sample, therefore the method enables in situ measurements.

Figure 9A:
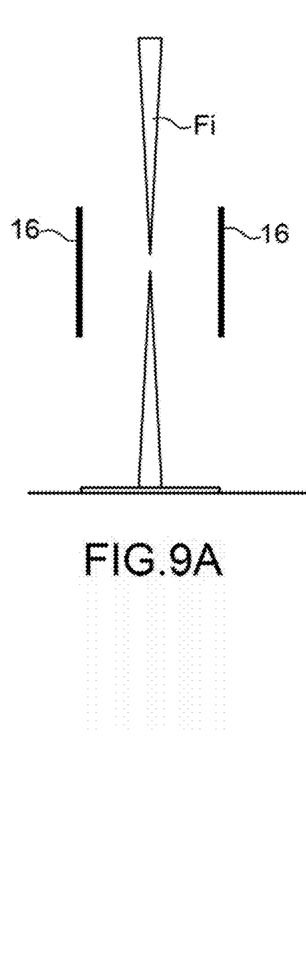
FIGS. 9A to 9C are diagrammatic views of an example of a method of measuring the dielectric constant of a fluid.
Figure 9B:
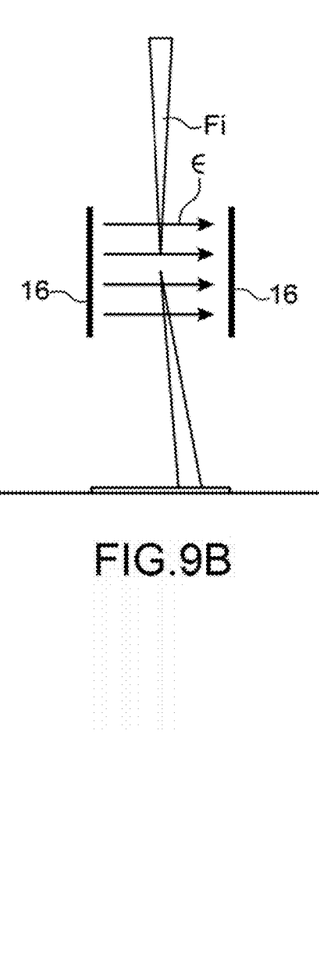
Figure 9C:
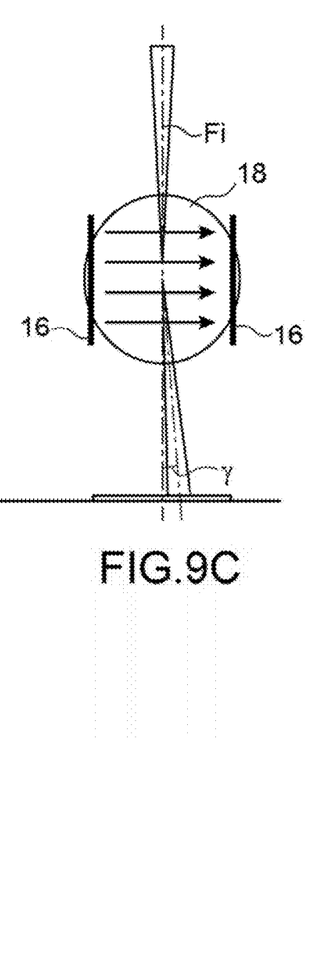

The method according to the invention can be applied by creating an electric field in a fluid. FIGS. 9A to 9C show an example of an experiment in which the dielectric constant of a fluid can be determined using the method according to the invention, by creating an electric field in the fluid.

On FIG. 9A, there is a vacuum between the electrodes and no electric field is applied between the two electrodes 16. The incident beam Fi in precession mode is not deviated and it continues along the direction of the incident beam.

On FIG. 9B, an electric field E is applied between the two electrodes 16, which has the effect of deviating the electron beam in precession mode from the direction of the incident beam Fi.

On FIG. 9C, a liquid or gas fluid sample 18 is introduced between the two charged electrodes 16 to which an electric field E is applied. The fluid can be added between the electrodes of an electron microscope using a cell like that described in the document by E. A. Lewis et al 21. *Chemical Communication*, 2014, 50, 10019. As shown diagrammatically on FIG. 9C, the deviation of the electron beam will be different due to the presence of fluid that is not present on FIG. 9B, the value of the dielectric constant of the fluid being different from the value for a vacuum.

This deviation can be measured using the method according to the invention.

Figure 10A:
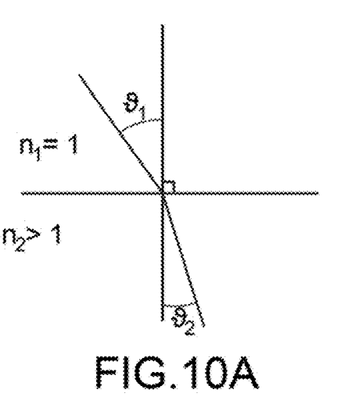
FIGS. 10A to 10C are diagrammatic views of optical diagrams illustrating application of this method to determination of the bevel angle of a sample knowing the local electric field of the sample or determination of the local electric field of the sample knowing the bevel angle of the sample.
Figure 10B:
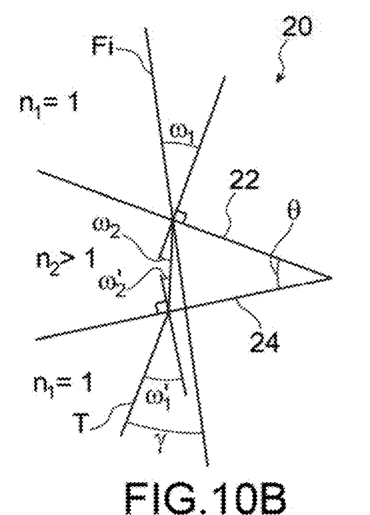
Figure 10C:
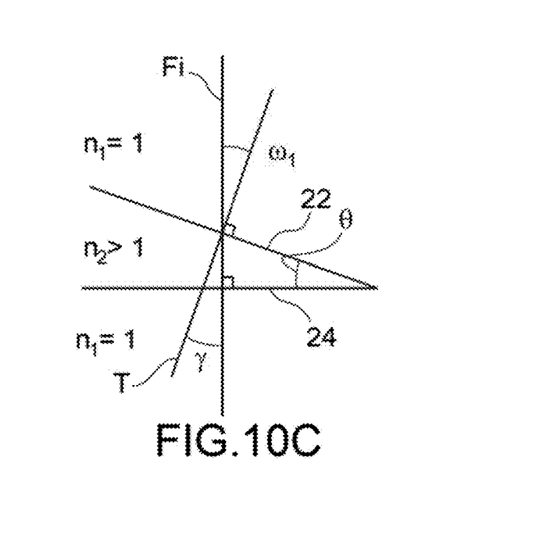

It is also possible to determine the bevel angle θ of a sample (see FIG. 10), knowing the local electric field in the sample. The bevel angle θ is the angle between the input face 22 of the incident beam Fi and the output face of the transmitted beam T.

According to Snell-Descartes' law for waves passing through an isotropic medium, the relation between the wave length λ, the refraction indices of medium $n_2$ and the exterior $n_1$ and the angles $\vartheta_1$ and $\vartheta_2$ of the incident beam and the transmitted beam relative to the normal to the faces (FIG. 10A) is as follows:

$$\frac{\sin\vartheta_1}{\sin\vartheta_2} = \frac{\lambda_1}{\lambda_2} = \frac{n_2}{n_1}$$

The refraction index is equal to 1 if the sample is placed in a high vacuum. For typical conditions, the refraction index $n_2$, denoted n in the following, is slightly more than 1 because it expresses the ratio of wave lengths for a electron in a vacuum and in the sample.

The local electric field φ in the sample that accelerates electrons when they pass through the sample is typically between 10 eV and 30 eV for solids.

Electron wave lengths λ can be expressed using Planck's constant h, the kinetic energy of the electron E and the mass at rest of electron $E_0$, using the following relation:

$$\lambda = \frac{hc}{\sqrt{2EE_0 + E^2}}$$

The refraction index n can then be written:

$$n = \frac{\lambda_1}{\lambda_2} = \sqrt{\frac{2(E+\Phi)E_0 + (E+\Phi)^2}{2EE_0 + E^2}}$$

The refraction index of a material with a local electric field of 20 eV for a beam of incident electrons accelerated by a voltage of 200 kV is equal to about: 1.000058.

In the case of a sample with a bevel angle, the angular deviation γ of the transmitted beam relative to the incident beam (FIG. 10B) can be expressed using the bevel angle Θ, the refraction index n of the sample and the deflection angle $\omega_1$ of the incident beam relative to the input face according to the following relation.

$$\gamma = \omega_1 + \arcsin\left(n\sin\left(\theta - \arcsin\left(\frac{\sin(\omega_1)}{n}\right)\right)\right) - \theta$$

For example (FIG. 10C), the bevel angle of a sample can be determined if the local electric field in the sample, for example 20 eV, and the energy of the electron beam, for example 200 kV, are known.

The output surface 24 through which the beam is transmitted is such that it is a crystallographic plane, for example a cleavage plane or a surface of the substrate. The lower face can then be made perfectly perpendicular to the incident beam by orienting the sample using diffraction patterns.

In this case, the angle between the normal to the input face and the incident beam is equal to the bevel angle $\omega_1=\Theta$.

The probe in a vacuum is recorded in the diffraction plane to measure the 0 position.

The sample is then placed along the path of the beam and the diffraction plane is recorded once again. The deflection of the beam is measured at 0.002 (33.5 μrad).

Numeric methods are used to estimate the bevel angle Θ at 30°.

Conversely, if the bevel angle is known and the local electric field is not known, the refraction index n can be obtained from the angle γ determined using the above equation. The local electric field ϕ can then be deduced.

The invention claimed is:

1. Determination method for determining deflection of an electron beam resulting from an electric field and/or a magnetic field and presence of a sample, the electron beam having an initial direction, comprising the following steps:
   a) placement of a sample and illumination of the sample by an electron beam in precession mode using an illumination device, at least one revolution being made between the electron beam and the sample,
   b) generation of at least one diffraction pattern,
   c) analysis of the at least one diffraction pattern to measure an offset of a disk corresponding to the electron beam and/or diffracted beams or a reflected beam, and
   d) determination of the deflection of the electron beam due to the sample relative to the initial direction from the offset of said disk obtained in step c).

2. The determination method according to claim 1, comprising a step e) prior to step c) to make at least one diffraction pattern in a vacuum or a diffraction pattern with another sample and in which the offset in step c) is obtained by comparing the diffraction patterns of steps b) and e).

3. The determination method according to claim 1 in which, in precession mode, the electron beam forms an angle of between 0.01° and 10°.

4. The determination method according to claim 3 in which, in precession mode, the angle of the electron beam varies.

5. The determination method according to claim 1, in which each diffraction pattern is produced using data supplied during at least one revolution.

6. The determination method according to claim 1, comprising a step a1) between steps a) and b) of dynamic compensation of tilt due to precession mode.

7. The determination method according to claim 1, comprising a step e) prior to step c) to make at least one diffraction pattern in a vacuum or a diffraction pattern with another sample and in which the offset in step c) is obtained by comparing the diffraction patterns of steps b) and e) and in which step c) applies a cross correlation to determine the offset.

8. The determination method according to claim 1, in which, during step a), a diameter of the electron beam is between 0.1 nm and 100 nm.

9. The determination method according to claim 1, in which, during step a), an energy of the electron beam is between 1 keV and several MeV.

10. The determination method according to claim 1, in which steps a), b), c) and d) are done in n zones of the sample.

11. The determination method according to claim 10 comprising a step e) prior to step c) to make at least one diffraction pattern in a vacuum or a diffraction pattern with another sample and in which the offset in step c) is obtained by comparing the diffraction patterns of steps b) and e), and in which step e) is done in p zones, where p is less than n, and in which a step to extrapolate to n zones is done.

12. The determination method according to claim 1, in which during step c), offsets between two orthogonal directions are measured.

13. A method of determining a value of a local electric field and/or a value of a local magnetic field of said sample applying the determination method according to claim 1, comprising a step f) to determine the local electric field and/or the local magnetic field of said sample starting from an angle determined in step d).

14. A method of determining the value of the local electric field and/or the value of the local magnetic field of said sample according to claim 13, said sample comprising a bevel angle with a known value, comprising a step to determine an optical index of the sample from a value of a deflection angle of the electron beam and a step to calculate the value of the local electric field and/or the value of the local magnetic field from a value of the optical index and the bevel angle.

15. A method of determining properties of the sample by applying the determination method according to claim 1.

16. The method of determining properties of the sample by applying the determination method according to claim 15, comprising determining at least one of a dielectric constant of the sample, an internal potential of the sample, the electric field and the magnetic field.

17. A method of analysing a sample including, simultaneously, application of the determination method according claim 1, and performing an EDX experiment.

18. A method of determining a dielectric constant of a liquid sample applying the determination method according to claim 1, including applying at least one of an electric field a magnetic field with known values.

19. A method of determining a bevel angle of a sample applying the determination method according to claim 1, using at least one of a predetermined value of the local electric field and a predetermined value of the local magnetic field of the sample.

20. The determination method according to claim 1, in which each diffraction pattern is produced using data supplied during a plurality of revolutions.

* * * * *